(12) United States Patent
Witte et al.

(10) Patent No.: US 10,258,967 B2
(45) Date of Patent: Apr. 16, 2019

(54) PT AND/OR PD EGG-SHELL CATALYST AND USE THEREOF

(71) Applicant: BASF Corporation, Florham Park, NJ (US)

(72) Inventors: Peter Witte, Utrecht (NL); Lei Zhang, De Meern (NL); Robert Terorde, Maarn (NL)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 15/559,458

(22) PCT Filed: Mar. 18, 2016

(86) PCT No.: PCT/IB2016/051547
§ 371 (c)(1),
(2) Date: Sep. 19, 2017

(87) PCT Pub. No.: WO2016/151454
PCT Pub. Date: Sep. 29, 2016

(65) Prior Publication Data
US 2018/0117566 A1 May 3, 2018

(30) Foreign Application Priority Data

Mar. 20, 2015 (NL) ..................................... 2014493
Dec. 22, 2015 (NL) ..................................... 2016001

(51) Int. Cl.
| | |
|---|---|
| *C07C 29/17* | (2006.01) |
| *B01J 23/00* | (2006.01) |
| *B01J 21/00* | (2006.01) |
| *B01J 31/00* | (2006.01) |
| *B01J 37/00* | (2006.01) |
| *B01J 35/00* | (2006.01) |
| *B01J 23/44* | (2006.01) |
| *B01J 37/03* | (2006.01) |
| *B01J 37/16* | (2006.01) |
| *B01J 37/02* | (2006.01) |
| *B01J 21/18* | (2006.01) |
| *B01J 23/42* | (2006.01) |
| *B01J 23/52* | (2006.01) |
| *B01J 35/02* | (2006.01) |
| *B01J 35/10* | (2006.01) |

(52) U.S. Cl.
CPC ............... *B01J 23/44* (2013.01); *B01J 21/18* (2013.01); *B01J 23/42* (2013.01); *B01J 23/52* (2013.01); *B01J 35/0006* (2013.01); *B01J 35/006* (2013.01); *B01J 35/008* (2013.01); *B01J 35/0013* (2013.01); *B01J 35/0066* (2013.01); *B01J 35/023* (2013.01); *B01J 35/026* (2013.01); *B01J 35/1014* (2013.01); *B01J 35/1019* (2013.01); *B01J 35/1023* (2013.01); *B01J 35/1028* (2013.01); *B01J 37/0203* (2013.01); *B01J 37/0211* (2013.01); *B01J 37/0219* (2013.01); *B01J 37/0221* (2013.01); *B01J 37/031* (2013.01); *B01J 37/035* (2013.01); *B01J 37/038* (2013.01); *B01J 37/16* (2013.01); *C07C 29/17* (2013.01)

(58) Field of Classification Search
CPC .. C07C 29/17; B01J 23/42; B01J 23/44; B01J 21/18; B01J 35/00; B01J 31/28
See application file for complete search history.

(56) References Cited

U.S. PATENT DOCUMENTS

| | | |
|---|---|---|
| 4,212,824 A | 7/1980 | Seagraves |
| 4,361,500 A | 11/1982 | Máthe et al. |
| 6,090,746 A | 7/2000 | Bönnemann et al. |
| 2002/0151433 A1 | 10/2002 | Yoshihara et al. |
| 2009/0047559 A1 | 2/2009 | Terada et al. |
| 2011/0015451 A1 | 1/2011 | Witte |
| 2011/0033353 A1 | 2/2011 | Siani et al. |
| 2014/0044627 A1 | 2/2014 | Siani et al. |

FOREIGN PATENT DOCUMENTS

WO 2009/096783 A1 8/2009

OTHER PUBLICATIONS

U.S. Appl. No. 15/559,837, filed Sep. 20, 2017, Peter Witte, et al.
International Search Report and Written Opinion of the International Searching Authority dated Jun. 2, 2016 in PCT/IB2016/051547 filed Mar. 18, 2016.
Sebastian Storck, et al., "Characterization of Micro- and Mesoporous Solids by Physisorption Methods and Pore-Size Analysis" Applied Catalysis A: General, vol. 174, Issues 1-2, Nov. 16, 1998, pp. 137-146.
A. C Vermeulen, et al., "Hydrolysis-Precipitation Studies of Aluminum (III) Solutions. I. Titration of Acidified Aluminum Nitrate Solutions" Journal of Colloid and Interface Science, vol. 51, No. 3, Jun. 1975, pp. 449-458.
Peter T. Witte, et al., "NanoSelect Pd Catalysts: What Causes the High Selectivity of These Supported Colloidal Catalysts in Alkyne Semi-Hydrogenation?" ChemCatChem, vol. 5, Issue 2, Feb. 2013, pp. 582-587.
International Search Report dated Jun. 2, 2016 in PCT/IB2016/051547 filed Mar. 18, 2016.

*Primary Examiner* — Sikarl A Witherspoon
(74) *Attorney, Agent, or Firm* — Oblon, McClelland, Maier & Neustadt, L.L.P.

(57) ABSTRACT

The present invention is in the field of catalysis. More particularly, the present invention is directed to supported precious metal catalysts, preferably palladium and/or platinum metal catalysts, having a high metal loading, a high degree of dispersion and a high degree of edge-coating. The present invention is further directed to a process for producing these catalysts, as well as to the use of these catalysts in chemical reactions.

20 Claims, 3 Drawing Sheets

PT AND/OR PD EGG-SHELL CATALYST AND USE THEREOF

The present invention is in the field of catalysis. More particularly, the present invention is directed to supported precious metal catalysts, preferably palladium and/or platinum metal catalysts, having a high metal loading, a high degree of dispersion and a high degree of edge-coating. The present invention is further directed to a process for producing these catalysts, as well as to the use of these catalysts in chemical reactions.

Many supported precious metal (PM) catalysts are used inter alia for selective conversion of fine chemicals, which are typically highly functionalized large molecules. In order for the PM crystallites to be best accessible for the large molecules, it is desirable to have them situated in the outer shell of the support as much as possible. This is referred to as an edge-coated metal distribution. Typically a high degree of edge-coating is achieved when the majority of the PM crystallites are situated in the outer shell of the support. Such an edge-coated distribution has the additional advantage that the substrate molecule rapidly leaves the vicinity of the PM crystallite after it is converted, thereby minimizing any side reactions from taking place. However, the preparation of edge-coated catalysts with a high dispersion is difficult. Since only a small portion of the total surface area of the support is used, edge-coated catalysts generally have a low dispersion.

Supported PM catalysts are typically prepared by a deposition-reduction method, in which the metal is first deposited on a support and then reduced. In order to prepare a catalyst with a high dispersion typically a deposition-precipitation preparation procedure is carried out in which the metal salt has time to diffuse into the pores of the support. In this way, a high dispersion is achieved by the metal being distributed over the complete surface area of the support. This provides a large active metal surface area since the formed metal crystallites are very small, typically in the order of a few nanometers. On the other hand, for the preparation of edge-coated catalysts, the metal salt should not diffuse far into the pores of the support (i.e. typically less than 100 nm into the pores for a support particle having an average size of about 20 to 100 micron), but should deposit immediately upon contact with the support. These two methods contradict each other, so the preparation of high-dispersed edge-coated metal catalysts is typically a compromise between the two factors.

Preparing a supported PM catalyst with a low metal loading (i.e. typically less than 1 wt. % PM) potentially overcomes this problem, since the small amount of PM used can be easily accommodated in the outer shell of the support while maintaining a high dispersion. However, this has the disadvantage that it will lead to a PM catalyst with a low activity per gram of material. Although increasing the precious metal loading would overcome the low activity, maintaining both the high dispersion and high edge coating with the increased precious metal loading has proven to be difficult.

WO-A-2009/096783 describes the preparation of an aqueous colloidal precious metal suspension, which process comprises reducing a precious metal salt in aqueous solution using a functionalized, water soluble quaternary ammonium salt in the absence of organic solvents, to form elementary nanoparticles. Although this known method yields small metal particles, there is still a need for catalysts having even smaller metal crystallites, which are distributed as described above.

Also, the document of P. T. Witte, S. Boland, F. Kirby, R. van Maanen, B. F. Bleeker, D. A. M. de Winter, J. A. Post, J. W. Geus, P. H. Berben, Chem Cat Chem. 5 (2013) 582-587 describes heterogeneous catalysts based on colloidal suspensions which are characterized by small metal crystallite sizes (i.e. typically nanometer size).

The present invention aims at producing catalysts having even smaller precious metal particle (crystallite) sizes, in particular nanoparticles that are about the same size and/or smaller than the average pore size of the support. Furthermore, the present invention aims at producing catalysts wherein the supports are edge coated with the crystallites and wherein the catalysts have a high metal loading (i.e. typically 1.0 wt. % or more PM).

In U.S. Pat. No. 4,212,824 a platinum on a carbon black support catalyst is described with an improved metal distribution, as determined by ESCA (electron spectroscopy for chemical analysis). However, U.S. Pat. No. 4,212,824 does not specify the metal dispersion of the catalyst. Further, the carbon black support used in U.S. Pat. No. 4,212,824 has a low surface area (i.e. 20-100 $m^2/g$).

Accordingly it is a first object of the present invention to provide a precious metal catalyst, in particular a palladium and/or platinum metal catalyst, which is not only both edge coated and has a high metal dispersion, but also has a high metal loading. Another object of the present invention is to provide a process for producing said catalyst. A further object of the present invention is to provide said catalyst, so that it may be used in chemical reactions.

Surprisingly it has been found that the edge-coating and metal dispersion of the catalyst can be controlled separately. As a result, both parameters can be optimized separately to obtain highly dispersed edge coated precious metal catalysts, in particular palladium and/or platinum metal catalysts, which also have a high metal loading, according to the present invention.

The present invention is accordingly directed to a precious metal catalyst, wherein said catalyst comprises nanocrystallites of a precious metal on a powder support, wherein the nanocrystallites have an average size of less than 5 nm, wherein the catalyst comprises at least 1.0 wt. % precious metal, based on the weight of the catalyst, and wherein the precious metal is palladium and/or platinum metal;

wherein the palladium metal catalyst has a surface enrichment value of from at least 6.5 to at most 150; and, wherein the platinum metal catalyst has a surface enrichment value of from at least 1.5 to at most 150.

Figure 1:
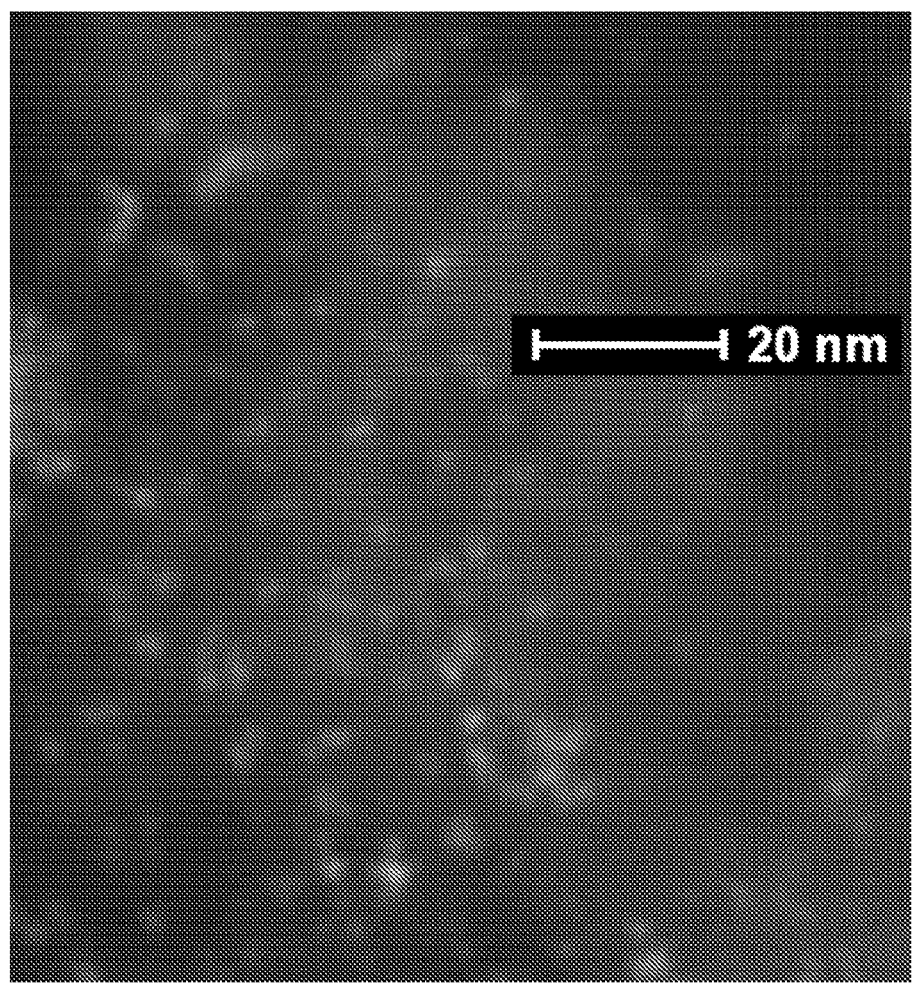
FIG. 1 shows TEM analysis of the catalyst showed the formation of 2 nm Pt crystallites.

The precious metal catalyst of the present invention typically comprises nanocrystallites of precious metal, in particular palladium and/or platinum metal, having an average size of from 1 to less than 5 nm, preferably between 1 and 4 nm, and more preferably between 1.5 and 3 nm.

The average size of the precious metal nanocrystallites, as used herein, is based on the value that can be determined by Transmission Electron Microscopy (TEM), unless otherwise indicated. Typically, for every measurement at least 200 PM crystallites are counted.

Typically, a palladium metal catalyst of the present invention has a surface enrichment value of at least 6.5, preferably at least 8 and more preferably at least 10. The surface enrichment value of the palladium metal catalyst is typically at most 150, preferably at most 120, and more preferably at most 90.

A platinum metal catalyst of the present invention typically has a surface enrichment value of at least 1.5, preferably at least 2 and more preferably at least 4. Typically, the surface enrichment value of the platinum metal catalyst is at most 150, preferably at most 120, and more preferably at most 90.

The surface enrichment value (SEV) can be determined by using X-ray photoelectron spectroscopy (XPS) and inductively coupled plasma (ICP) measurements, in particular inductively coupled plasma optical emission spectrometry (ICP-OES) measurements, and the following formula (I):

$$SEV = (XPS\ wt.\ \% - ICP\ wt.\ \%)/ICP\ wt.\ \% \quad (I)$$

wherein XPS wt. % is the XPS measurement and ICP wt. % is the ICP measurement (i.e. ICP-OES measurement) of the PM content of the catalyst according to the present invention, in weight percent (wt. %). XPS measurements are used to determine the content of the precious metal in the outer shell of the powder support (i.e. typically about 0 to 10 nm in depth from the surface of the powder support particle in weight percent (wt. %). ICP measurements (i.e. ICP-OES measurements) are used to determine the precious metal content in the catalyst powder support (i.e. a bulk measurement), in weight percent (wt. %).

In the case of a perfectly uniform distribution of precious metal on the powder support the precious metal content as determined by XPS and ICP measurements (i.e. ICP-OES measurements) would be substantially the same and would result in a surface enrichment value of about zero. For an edge-coated metal distribution, the precious metal content in the outer shell of the catalyst powder support, as determined by XPS measurement, should be considerably higher than that in the powder support, as determined by ICP measurement (i.e. ICP-OES measurements). The reason that XPS measurements only give information on the outer few nanometers (i.e. typically on the outer shell of 5-10 nm of the surface of the measured material) of the measured material, is that although the X rays penetrate deep into a material, the released photoelectrons will only be measured if they have enough energy to escape from the material. The released photoelectrons can undergo inelastic collisions, recombination, excitation of the sample, recapture or trapping in various excited states within the material, all of which can reduce the number of escaping photoelectrons. These effects appear as an exponential attenuation function as the depth increases, making the signals detected from elements at the surface much stronger than the signals detected from elements deeper below the material surface. Therefore, an XPS measurement typically only gives information on the outer few nanometers of the measured material.

Unless explicitly indicated otherwise, all ICP measurements (i.e. ICP-OES measurements) of the catalysts, as used herein, are the values that can be measured on a Thermo Scientific™ iCAP™ 7400 ICP-OES Analyzer having an aerosol concentric nebulizer, using the autosampler CETAC ASX-260 and typically calibration curves of 0-25 ppm. Two standard series typically used were of 0 ppm (blank); 5, 10 and 25 ppm of the elements Pd, Pt, Rh, and Ru, with each element having the same concentration, and with one of the series in an aqueous solution of 10 wt. % nitric acid (concentration of 65 wt. %) and the other series in an aqueous solution of 15 wt. % of $H_3PO_4/H_2SO_4$ (5:3) ($H_3PO_4$ having a concentration of 85 wt. %, and, $H_2SO_4$ having a concentration 98 wt. %. Typically all measurement series performed started with the standards, so as to determine the calibration curve and ensure that the correlation coefficient was greater than 0.999. The standard of 10 ppm was usually used as an internal standard during a series measurement.

All XPS measurements of the catalysts, as used herein, unless explicitly indicated otherwise, are the values that can be measured using a Phi Versa Probe 5000 spectrometer using monochromatic Al Kα radiation (80 W). The instrument work function was calibrated to give a binding energy (BE) of 84.0 eV for the Au 4f7/2 line of metallic gold and the spectrometer dispersion was adjusted to give a BE of 932.6 eV for the Cu 2p3/2 line of metallic copper. The built in Phi charge neutralizer system was used on all samples measured. To minimize the effects of differential charging, all catalyst samples were usually mounted and insulated against the ground. Typically, the catalyst samples were prepared as a thin powder film on double-faced adhesive tape.

XPS survey scan analyses of the catalyst samples were typically carried out with an analysis area of 0.1×1.4 mm, a pass energy of 117 eV and an energy step size of 0.5 eV. High resolution analyses were usually carried out on the same analysis area with a pass energy of 23.5 eV and an energy step size of 0.1 eV. Three XPS measurements were usually made per catalyst sample. Energy correction of the spectra obtained was usually performed in such a manner, that the position of the 1 s-signal of C was at a binding energy of 284.5 eV.

Quantification of elemental abundance was usually determined from the XPS survey spectra by employing a Shirley background subtraction and using the transmission function correction and elemental sensitivity factors provided by the manufacturer of the above-mentioned spectrometer. The concentration of an element determined in atomic % was converted into mass (i.e. weight) % using the following formula (II):

$$C(\text{Element})[\text{mass-}\%] = \frac{C(\text{Element})[at\text{-}\%] \times M(\text{Element})\left[\frac{g}{mol}\right]}{\Sigma_{all\ elements} C(\text{Element})[at\text{-}\%] \times M(\text{Element})\left[\frac{g}{mol}\right]} \times 100 \quad (II)$$

wherein C(Element)[mass-%] is the concentration of the element in mass (i.e. weight %), C(Element)[at-%] is the concentration of an element in atomic %, and M(Element)[g/mol] is the molar mass of an element in g/mol.

Surprisingly it has been found that the catalyst of the present invention has a high activity due to a combination of the high metal dispersion, which increases the number of active sites available to the reactants as well as the contribution of atoms at the corners or edges of the metal nanocrystallites, a high edge-coating, which leads to improved accessibility for reactants to the catalytic metal surface, and high metal loading, which leads to a high activity per gram of material. The catalyst of the present invention also surprisingly has the advantage of a high selectivity due to the edge-coating which decreases the likelihood of undesirable side reactions. A further advantage of the catalyst of the present invention is that internal heat transfer problems will not occur when it is used in an exothermic chemical reaction, because the precious metal is present mostly on the surface of the support. Therefore any heat that is generated during the chemical reaction is able to be easily transferred into the surrounding reaction mixture.

A palladium metal catalyst of the present invention typically comprises palladium metal in an amount of between 1.0 and 20 wt. %, preferably between 1.5 and 15 wt. %, and more preferably between 2.0 and 10 wt. %, based on the weight of the catalyst.

Typically a platinum metal catalyst of the present invention comprises platinum metal in an amount of between 1.0 and 20 wt. %, preferably between 1.5 and 15 wt. %, and more preferably between 2.0 and 10 wt. %, based on the weight of the catalyst.

All weight % referred to herein are based on the weight of the isolated and washed and dried catalyst, unless otherwise indicated.

The powder support of the catalyst of the present invention may be selected from the group consisting of silica, alumina, zirconia, titanium oxide, ceria, magnesium oxide, zinc oxide, metal silicates (e.g. titanium silicates (TiS)), metal aluminates, zeolites, carbon nanotubes, carbon nanofibres, graphitic carbon and activated carbon (AC) and combinations thereof, and preferably activated carbon.

In general, the BET surface area of the powder support is typically between 100 and 3000 $m^2/g$, preferably between 500 and 2500 $m^2/g$, and more preferably between 700 and 2000 $m^2/g$. For the oxidic supports the BET surface area is typically more than 50 $m^2/g$. Typically the BET surface area of the oxidic supports is less than 1000 $m^2/g$. The BET surface area of carbon based supports, such as activated carbon, have a higher BET surface area of typically more than 400 $m^2/g$. Typically the BET surface area of the carbon based supports, such as activated carbon, is less than 3000 $m^2/g$. The BET surface area, as used herein, is the value that can be measured by determining the amount of nitrogen adsorbed at 77 K and P/Po of approximately 0.3 and assuming a nitrogen cross sectional area of 16.2 $Å^2$, after degassing the sample at 180° C. on a Micromeritics ASAP 2420.

The micropore surface area of the powder support is typically between 10 and 1000 $m^2/g$, preferably between 20 and 750 $m^2/g$, and more preferably between 30 and 500 $m^2/g$. The micropore surface area, as used herein, is the value that can be determined from a t-plot analysis, as described in Applied Catalysis A: General 174(1998) 137-146 and determined using the suite of software programs on a Micromeritics ASAP 2040.

Typically, the powder support of the catalyst of the present invention is microporous and/or mesoporous.

Activated carbon is the preferred support to be used in the catalyst of the present invention since it has a high BET surface area, is economically cost effective, and allows easy recovery of the precious metal by simply oxidizing the catalyst at an elevated temperature.

Typically the Dv(90) particle size distribution of the powder support is between 1 and 500 micron, preferably between 5 and 300 micron, and more preferably between 10 and 200 micron. The Dv(90) particle size distribution is defined as meaning that 90% of the particles have a volume average particle size less than the value in the above-mentioned ranges indicated. The Dv(90) particle size distribution, as used herein, is the value that can be measured of a pre-sonicated sample mixture in water by light scattering using a Malvern Mastersizer 2000.

In an additional embodiment, the present invention is directed to a process for preparing a precious metal catalyst according to the present invention, wherein said process comprises the steps of:

reducing a precious metal compound in an aqueous solution by contacting said solution with a reducing agent, a stabilizing agent and optionally a coordinating agent to form a colloidal precious metal suspension;

contacting the suspension with a powder support at a pH value of between 9.5 and 11; and, recovering the precious metal catalyst.

The advantage of the process of the present invention is that the precious metal dispersion is set in the first step. This is done using a colloidal approach, in which the precious metal compound is reduced to precious metal crystallites in an aqueous solution in the presence of a reducing agent, a stabilizing agent and optionally a coordinating agent to form a colloidal suspension. Typically, the precious metal compound in the aqueous solution is contacted, in particular mixed, with the reducing agent, the stabilizing agent and optionally the coordinating agent. In the following step the edge coating and the precious metal loading on the powder support is set by adjusting the pH and depositing the resulting colloidal suspension onto a suitable powder support by contacting the suspension, in particular by mixing, with the support to obtain the catalyst of the present invention.

Preferably the precious metal is selected from platinum, palladium, iridium, rhodium, ruthenium, silver, gold and combinations thereof, and preferably palladium and/or platinum metal.

Suitable precious metal compounds which may be used in the process of the present invention include water soluble salts, such as nitrates, acetates, sulfates, ammonium citrates and chlorides and combinations thereof. Preferably, the salt used is a palladium and/or platinum metal salt. More preferably, the salt used is $Na_2PdCl_4$ and/or $H_2PtCl_6$.

The reducing agent and stabilizing agent, as used in the process of the present invention, may comprise of one compound or more than one compound, which acts as both a reducing agent and a stabilizing agent.

The reducing agent acts in the process of the invention to reduce the precious metal compound in an aqueous solution (i.e. precious metal ions) to precious metal particles.

The stabilizing agents acts in the process of the invention to stabilize the precious metal particles formed by contacting the precious metal compound with the reducing agent in an aqueous solution, thereby forming a colloidal precious metal suspension. The advantage of using a stabilizing agent according to the process of the invention is that it prevents or minimizes precious metal agglomeration and particle growth.

Suitable reducing agents which may be used in the process according to the present invention include a quaternary ammonium salt, sodium formate, formic acid, sodium citrate, citric acid, hydrazine, alcohols (e.g. typically $C_1$-$C_4$ alcohols but also diols or polyols), boro-hydrides, formaldehyde, hypophosphite, metal alkalydes, hydrogen and combinations thereof.

Preferably, the reducing agent is a quaternary ammonium salt, and more preferably is a functionalized quaternary ammonium salt. In this respect the functionalization comprises the presence of at least one reducing group, selected from the group consisting of primary alcohols, secondary alcohols, cyclohexenyl and combinations thereof, preferably in combination with at least one bulky group selected from the group consisting of $C_3^+$-alkyls (i.e. $C_4$-$C_{20}$ alkyls) cycloalkyl, aralkyl, alkaryl and aryl groups and combinations thereof, and wherein the at least one bulky group is optionally functionalized with at least one —OH and/or cyclohexynol group. In addition, the quaternary ammonium salt can be chiral, such as a quaternized cinchonine or cinchonidine.

Most preferably the quaternary ammonium salt which may be used in the process of the present invention is of the formula (III):

    RR'R''—N$^+$—CH$_2$CH$_2$OHX—    (III)

wherein R, R', and R'' are independently of each other $C_1$-alkyl and higher (i.e. $C_4$-$C_{20}$ alkyls), wherein the $C_1$-alkyl and higher (i.e. $C_4$-$C_{20}$ alkyls) are optionally functionalized with at least one —OH and/or cyclohexynol group, and X is Cl$^-$, Br$^-$, H$_2$PO$_4^-$, NO$_3^-$ or HSO$_4^-$. Preferably, R and R' are $C_1$-alkyl, and R'' is selected from $C_3$-alkyl and higher (i.e. $C_4$-$C_{20}$ alkyls), more preferably $C_{16}$-alkyl.

Typically, the amount of reducing agent used in the process according to the present invention is at least 3 molar equivalents, and preferably at least 5 molar equivalents, of the amount of the precious metal compound to be reduced. The amount of reducing agent typically used in the process of the present invention is at most 40 molar equivalents, and preferably at most 25 molar equivalents, of the amount of the precious metal to be reduced.

Suitable stabilizing agents which may be used in the process of the present invention include a quaternary ammonium salt, donor ligands (e.g. phosphines, amines and/or thioethers ligands), polymers (e.g. poly(vinylpyrrolidone) (PVP), poly(vinyl alcohol) (PVA), and/or poly(methylvinyl ether)), surfactants and combinations thereof, preferably is a quaternary ammonium salt, and more preferably is a functionalized quaternary ammonium salt, wherein the functionalization is according to that as described herein above.

Typically, the amount of stabilizing agent used in the process according to the present invention is at least 3 molar equivalents, and preferably at least 5 molar equivalents, of the amount of the precious metal compound to be reduced. The amount of stabilizing agent typically used in the process of the present invention is at most 25 molar equivalents, and preferably at most 10 molar equivalents, of the amount of the precious metal compound to be reduced.

The advantage of using a quaternary ammonium salt as a reducing agent is that it also acts as a stabilizing agent which minimizes the number of reagents used in the process according to the present invention. A further advantage is that most of the reducing agents described are volatile or produce volatile products, while a quaternary ammonium salt, which is basically an ionic liquid, has no vapor pressure and can be used in production without the necessary safety requirements that are needed for reducing agents, such as low boiling organic solvents.

The coordinating agent acts in the process of the invention to coordinate to the precious metal compound in an aqueous solution during the reduction. The advantage of using a coordinating agent is that it results in a reduction in the size of the precious metal particles produced (i.e. higher dispersion), in comparison to when no coordinating agent is used.

A coordinating agent which may optionally be used in the process of the present invention is urea and/or ammonia.

Preferably, a coordinating agent is used in the reduction step of the process of the present invention when the precious metal compound to be reduced is a palladium and/or gold metal compound, optionally in combination with one or more other precious metal compounds.

The amount of a coordinating agent which may be used in the process of the present invention is typically 0.5 or more molar equivalents of the amount of the precious metal compound to be reduced. The amount of coordinating agent typically used in the process of the present invention is at most 25 molar equivalents of the amount of the precious metal compound to be reduced. Preferably, the amount of coordinating agent used in the process of the present invention is 0.5-15 molar equivalents of the amount of the precious metal compound to be reduced. Even more preferably, the amount of coordinating agent used in the process of the present invention is 1-15 molar equivalents of the amount of the precious metal compound to be reduced.

Suitable concentrations of the precious metal solutions which may be used in the process of the present invention are preferably 0.1-10 g/L, more preferably 0.1-8 g/L and even more preferably 0.2-5 g/L, wherein the g/L is based on the weight of the PM in the PM compound used.

The use of urea to prepare supported metal catalysts by a so-called homogeneous deposition-precipitation method has been described in literature, see for instance A. C. Vermeulen, J. W. Geus, R. J. Stol and P. L. de Bruyn, *J. Colloid and Interface Science* 51(1975)449). In this method the metal and support are mixed and heated in the presence of urea. This results in the hydrolysis of urea to the basic species of $CO_2$ and $NH_3$ which causes the pH to rise, and the subsequent deposition of the metal species onto the support. Addition of the basic species to the reaction mixture is not performed since it causes an inhomogeneous increase of the pH. The deposited metal species is reduced in a subsequent step.

In the process of the present invention the coordinating agent is not added in the deposition step, but optionally added in the reduction step. Surprisingly it has been found that urea and/or ammonia acts as a coordinating agent for the reduction of the precious metal compound, in particular for palladium and gold metal compounds, which is indicated by the higher temperature that is required for the metal reduction to take place.

Suitable temperatures for the solutions used in the reduction step of the process of the present invention typically range from between 10 to 95° C. Preferably, the temperature used in the reduction step is 10 to 50° C. when reducing a gold metal compound; or, the temperature used in the reduction step is 50 to 95° C. when reducing a palladium and/or platinum metal compound. The deposition step may suitably be carried out at a temperature of 10 to 50° C.

The reduction process step is preferably carried out at a pH of between about 2 and 11. More preferably the reduction step is carried out at a pH of between 2 and 6 when reducing a palladium and/or platinum metal compound; or, at a pH of between 8.5 and 10.5 when reducing a gold metal compound. If necessary, the pH can be adjusted during the reduction step by the addition of a base e.g. an alkali metal carbonate (such as $Na_2CO_3$) or an alkali metal hydroxide (such as NaOH).

The deposition step of the process of the present invention is typically carried out of a pH of between 9.5 and 11, and preferably between 9.5 and 10.5. The pH can also be adjusted during the deposition step by the addition of a base e.g. an alkali metal carbonate (such as $Na_2CO_3$) or an alkali metal hydroxide (such as NaOH).

The deposition step is typically carried out at a temperature between 20-95° C., preferably between 20-75° C. and most preferably between 20-50° C.

Surprisingly it has been found that by adjusting the pH during the deposition step to a value of between 9.5 and 11, the amount of precious metal colloid deposited on the powder support can be increased, while maintaining the stability of the PM colloidal suspension. Advantageously, the deposition happens in such a way that the precious metal deposited is accessible to chemical reactants since it is deposited on the outer shell of the powder support particles, thereby ensuring an efficient access to the catalytically active surface area. Furthermore, the precious metal crystallites are typically distributed in a more uniform manner over the support surface with less agglomeration occurring when compared to a deposition carried out at a lower pH.

The catalyst of the invention may be recovered by suitable separation means, such as, filtration and/or centrifugation. Typically the separated catalyst is then washed with water. The removal of any halides present, such as chloride ions, can be monitored during the washing step by an indicator test using a $AgNO_3$ solution.

In a further embodiment, the precious metal catalyst of the present invention, preferably a palladium and/or platinum metal catalyst, may be used generally for all chemical reactions for which precious metal catalysts are suitable. Such reactions may include isomerization, oxidation, hydrogenolysis (e.g. hydro-desulfurization), hydrogenation/dehydrogenation and hydro-dewaxing reactions.

These reactions may conveniently be carried out in slurry phase or in a fixed bed in an organic solvent and optionally in the presence of hydrogen, in particular when carrying out hydrogenation reactions either in a three phase system or in a two phase system, where the hydrogen is dissolved in the organic solvent.

For the purpose of clarity and a concise description, features are described herein as part of the same or separate embodiments, however, it will be appreciated that the scope of the invention may include embodiments having combinations of all or some of the features described.

The present invention is now elucidated on the basis of some examples, which are not intended to limit the scope of the invention.

EXAMPLES

Example 1: Preparation of 2.43 wt. % Pt Supported on Activated Carbon Having Pt Metal Crystallites with an Average Size of 2 nm A 5 L beaker was equipped with baffles and filled with 3.6 L water at room temperature (i.e. 20-25° C.). Using a top stirrer, the water was stirred at 300 rpm. The water was heated to 95° C. The reducing/stabilizing agent (240 mL 30 wt. % Luviquat Mono CP (hydroxyethyl cetyldimonium phosphate) in water, obtained from Sigma-Aldrich) was added in one portion and the mixture was stirred for several minutes. A Pt solution (22.8 g 21.01 wt. % Pt as $H_2PtCl_6$ diluted to 300 mL by addition of water) was added to the mixture over a period of 10 min. After the addition of the Pt solution the pH was set to 5.0 by the addition of NaOH solution (10 wt. % NaOH in water). The mixture was stirred at 95° C. for two hours, while keeping the water level constant and while re-setting the pH to 5.0 every 30 min. After cooling, the pH of the colloidal Pt metal suspension was 4.9.

A 500 mL beaker was equipped with baffles, filled with 10 g (dry weight) of activated carbon powder (Dv(90) of 82 micron; BET surface area of 1432 $m^2/g$; and micropore surface area of 171 $m^2/g$) and 100 mL water at room temperature (i.e. 20-25° C.) was slowly added to prevent dust formation. Using a top stirrer, the slurry mixture was stirred at 300 rpm. By addition of NaOH solution (10 wt. % NaOH in water) the pH was set to 10.0 and the slurry mixture was stirred for one hour to obtain a homogeneous suspension. An amount of colloidal Pt suspension corresponding to 0.4 g Pt was added to this suspension over a period of 60 min. The pH was re-set to 10.0 by the addition of NaOH solution (10 wt. % NaOH in water) and the slurry mixture was stirred for 1 hour. The resulting Pt/AC catalyst was filtered off and washed with water until no more Cl was found in the washing water (indicator test using $AgNO_3$ solution). TEM analysis of the catalyst showed the formation of 2 nm Pt crystallites (see FIG. 1). ICP analysis determined that the catalyst had a Pt loading of 2.43 wt. %.

Example 2: Preparation of 1.29 wt. % Pd Supported on Activated Carbon Catalyst Having Pd Metal Crystallites with an Average Size of 2 nm A 5 L beaker was equipped with baffles and filled with 3.6 L water at room temperature (i.e. 20-25° C.). Using a top stirrer, the water was stirred at 300 rpm. The reducing/stabilizing agent (200 mL 30 wt. % Luviquat Mono CP (hydroxyethyl cetyldimonium phosphate) in water, obtained from Sigma-Aldrich) and the coordinating agent (2.0 g urea) were added in one portion and the mixture was stirred for several minutes. A Pd solution (10.5 g 18.98 wt. % Pd as $Na_2PdCl_4$ diluted to 500 mL by addition of water) was added to the mixture over a period of 30 min, during which the pH of the solution slowly dropped from 5.4 to 4.9. After the Pd addition the pH was set to 5.0 by addition of a few drops of NaOH solution (10 wt. % NaOH in water). The mixture was heated to 95° C. (pH 4.7) and kept at this temperature for two hours, while keeping the water level constant. After cooling the pH of the colloidal Pd suspension was 4.9.

Figure 2:
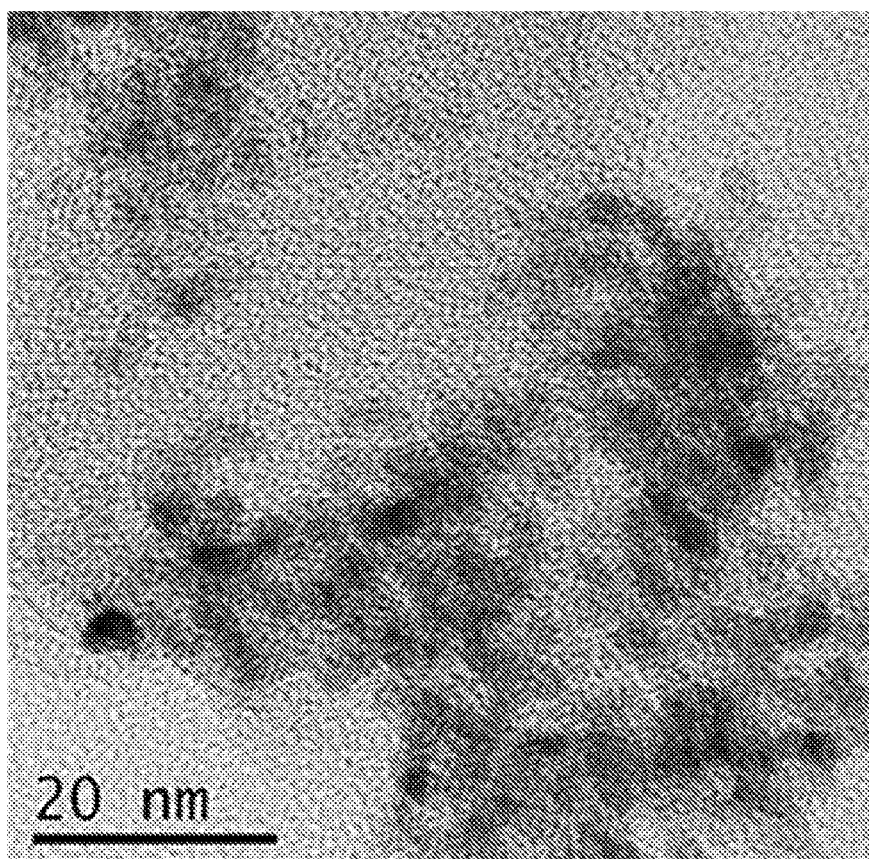
FIG. 2 shows TEM analysis of the catalyst showed the formation of 2 nm Pd crystallites.

A 800 mL beaker was equipped with baffles, filled with 20 g (dry weight) of activated carbon powder (Dv(90) of 82 micron; BET surface area of 1432 $m^2/g$; and micropore surface area of 171 $m^2/g$) and 200 mL water at room temperature (i.e. 20-25° C.) was slowly added to prevent dust formation. Using a top stirrer, the slurry mixture was stirred at 500 rpm. By addition of NaOH solution (10 wt. % in water) the pH was set to 10.0 and the mixture was stirred for one hour to obtain a homogeneous suspension. An amount of colloidal Pd suspension corresponding to 0.4 g Pd was added to this suspension over a period of 60 min. The pH was re-set to 10.0 by the addition of NaOH solution (10 wt. % NaOH in water) and the mixture was stirred for one hour. The resulting Pd/AC catalyst was filtered off and washed with water until no more Cl was found in the washing water (indicator test using $AgNO_3$ solution). TEM analysis of the catalyst showed the formation of 2 nm Pd crystallites (see FIG. 2). ICP analysis determined that the catalyst had a Pd loading of 1.29 wt. %.

Example 3 (Comparative): Preparation of 0.64 wt. % Pd Supported on Activated Carbon Having Pd Metal Crystallites with an Average Size of 2 nm, without Adjusting the pH in the Deposition Step An experiment is conducted with identical amounts as described in Experiment 2, only without the pH adjustment in the deposition step of Pd on AC. After the filtration step a darkly colored filtrate is observed. ICP analysis of the washed catalyst determined that the catalyst had a Pd loading of 0.64 wt. %.

Example 4: Analyses of Catalysts

The following properties of a catalyst according to the present invention (Examples 1 and 2) were determined and are shown in Table 1.

The ICP measurement was obtained as described hereinabove.

The PM crystallite sizes mentioned above for the Examples 1 and 2 and in Table 1 below were measured using TEM. Samples of the catalysts were prepared by first dispersing each of the catalyst in ethanol and applying the resulting dispersions between objective slides which produced a thin film. An ultra-thin carbon TEM carrier was then contacted with each of the thin films.

The prepared samples of the catalysts were investigated using a Tecnai G2-F20ST machine (FEI Company, Hillsboro, USA) operated at 200 keV. Energy Dispersive X-ray spectroscopy (EDXS) was applied to determine chemical compositions at distinct locations of the sample using an EDXi-detection system with an energy resolution of 131 eV at Mn—Kα (EDAX, Mahwah, USA). Images and spectroscopy data were evaluated using the Olympus iTEM 5.2 (Build 3554) (Olympus, Tokyo, Japan) and FEI TIA 4.1.202 (FEI Company, Hillsboro, USA) software packages. For PM crystallite size determination the microscopes magnification was calibrated using a MAG*I*CAL calibration sample (Technoorg Linda Ltd., Budapest, Hungary). The average PM crystallite size was determined by manually measuring the smallest diameter of about 200 PM crystallites per sample using the Olympus iTEM 5.2 software.

The XPS measurement was obtained as described hereinabove.

The surface enrichment value (SEV) was determined using the above-mentioned formula (I).

The following commercially available catalysts of Escat™ 1421 (Pd 5 wt. % on AC, reduced, from STREM Chemicals, Inc.), Escat™ 1621 (Pd 5 wt. % on AC, reduced, from STREM Chemicals, Inc.), Escat™ 1911 (Pd 3 wt. % on AC, reduced, from STREM Chemicals, Inc.), Escat™ 1941 (Pd 5 wt. % on AC, reduced, from STREM Chemicals, Inc.), Escat™ 1971(Pd 5 wt. % on AC, reduced, from STREM Chemicals, Inc.), Escat™ 2421(Pt 5 wt. % on AC, reduced, from STREM Chemicals, Inc.), Escat™ 2431(Pt 5 wt. % on AC, reduced, from STREM Chemicals, Inc.), Escat™ 2441 (Pt 5 wt. % on AC, unreduced, from STREM Chemicals, Inc.), F101 (Pt 5 wt. % on AC, reduced, from Sigma-Aldrich), Noblyst P2060 (Pt 5 wt. % on AC, reduced, from STREM Chemicals, Inc.) and Noblyst P2058 (Pt 5 wt. % on AC, reduced, from STREM Chemicals, Inc.) were similarly analyzed, with the exception that the Pd and Pt crystallite size were measured using CO chemisorption using an Autochem II 2920 Chemisorption Analyzer from Micromeritics Instrument Corporation. The results of these analyses are also shown in Table 1 below.

The CO chemisorption measurements of the above-mentioned commercially available catalysts were made using an Autochem II 2920 Chemisorption Analyzer from Micromeritics Instrument Corporation. The catalyst samples were prepared by drying the catalysts at 105° C. overnight to remove adsorbed water and other volatiles. The dried catalysts were loaded in amounts of about 0.1 to 0.2 g each into a sample tube. The catalyst samples were then pretreated with $H_2$ in Ar: 15 vol. % gas flow (50 mL/min) and a temperature ramp rate of 10° C./min to 200° C., and was held at a temperature of 200° C. for 30 min. The catalyst samples were then cooled under He gas flow (50 mL/min) to 50° C. A CO pulse (loop volume 0.39 mL STP) was injected into the He gas flow (50 mL/min) for 6 times with an interval of 5 min. Lastly, the catalyst samples were flushed with a He gas flow (50 mL/min) for 3 min. The effective metallic surface area per gram of PM and the average size of the PM nanocrystallites were determined using the data measured from the catalyst samples and the integrated software package of the Autochem II 2920 Chemisorption Analyzer.

TABLE 1

Characteristics of various catalysts

| Catalyst | Crystallite size (nm) | XPS (wt. %) | ICP (wt. %) | SEV |
|---|---|---|---|---|
| Example 1 | 2* (Pt) | 53.7 | 2.43 | 21 |
| Example 2 | 2* (Pd) | 27.4 | 1.29 | 20 |
| Escat ™ 1421 | 4.3# (Pd) | 14.4 | 5 | 1.9 |
| Escat ™ 1621 | 4.0# (Pd) | 17.8 | 5 | 2.6 |
| Escat ™ 1911 | 3.0# (Pd) | 21.0 | 3 | 6.0 |
| Escat ™ 1941 | 5.2# (Pd) | 24.1 | 5 | 3.8 |
| Escat ™ 1971 | 4.3# (Pd) | 17.3 | 5 | 2.5 |
| Escat ™ 2421 | 4.6# (Pt) | 9.3 | 5 | 0.9 |
| Escat ™ 2431 | 4.5# (Pt) | 10.4 | 5 | 1.1 |
| Escat ™ 2441 | 3.3# (Pt) | 11.1 | 5 | 1.2 |
| F101 | 5.2# (Pt) | 8.7 | 5 | 0.7 |
| Noblyst P2060 | 3.7# (Pt) | 8.2 | 5 | 0.6 |
| Noblyst P2058 | 4.9# (Pt) | 11.8 | 5 | 1.4 |

*as determined by TEM
as determined by CO chemisorption

Example 5: Semi-hydrogenation of 3-hexyn-1-ol Using a Supported Palladium Catalyst A 250 mL stainless steel autoclave was charged separately with 97 mg (dry weight) of the Pd/AC catalyst of Examples 2 and 3 and 100 g of a 4.5 wt. % solution of 3-hexyn-1-ol in 96 wt. % ethanol was added. The autoclave was closed and the mixture was heated to 30° C. with stirring. The stirring was stopped, and the air was replaced by flushing hydrogen over the mixture. After flushing the autoclave was pressurized with 3 bars of hydrogen. The stirring was resumed (1500 rpm) and the hydrogen consumption was recorded. After 90 min the stirring was stopped. The reaction rates r1 (semi-hydrogenation) and r2 (over-hydrogenation) are calculated in mL $H_2$ per min from the $H_2$ uptake curve.

Figure 3:
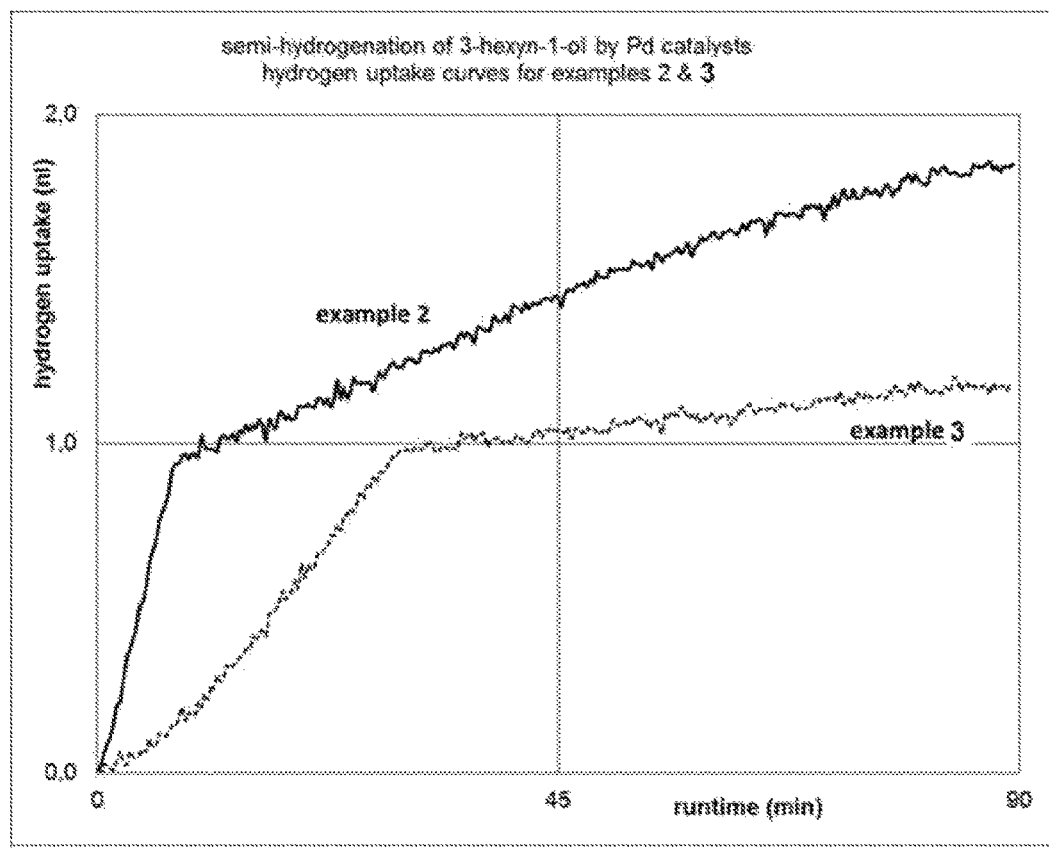
FIG. 3 shows the hydrogen uptake (nL) versus the runtime (min) using the catalyst according to the present invention of Example 2 (solid line) and the comparative catalyst of Example 3 (dotted line) in the semi-hydrogenation of 3-hexyn-1-ol.

FIG. 3 shows the hydrogen uptake (nL) versus the runtime (min) using the catalyst according to the present invention of Example 2 (solid line) and the comparative catalyst of Example 3 (dotted line) in the semi-hydrogenation of 3-hexyn-1-ol. Table 2 shows the r1 and r2 values (nL $H_2$ per min) as determined from the hydrogen uptake. The catalyst of the present invention in Example 2 had a r1 of 133 mL $H_2$ per min and the comparative catalyst of Example 3 had a r1 of 38 mL $H_2$ per min. This means that the increased metal loading of 100% led to an increase in the weight-based catalyst activity in the semi-hydrogenation of 250% without affecting the selectivity as calculated from the ratio of over-hydrogenation r2 over the semi-hydrogenation r1 (r2/r1=0.08 for Example 2 and 0.09 for Example 3).

TABLE 2

Performance data of catalysts Examples 2 and 3 in the selective hydrogenation of 3-hexyn-1-ol

| Catalyst | r1 (mL $H_2$ per min) | r2 (mL $H_2$ per min) | r2/r1 |
|---|---|---|---|
| Example 2 | 133 | 11.3 | 0.08 |
| Example 3 | 38 | 3.3 | 0.09 |

The invention claimed is:

1. A precious metal catalyst, wherein said catalyst comprises nanocrystallites of precious metal on a powder support, wherein the nanocrystallites have an average size of from 1 to less than 5 nm, wherein the catalyst comprises precious metal in an amount of at least 1.0 wt. %, based on the weight of the catalyst, and wherein the precious metal is palladium and/or platinum metal; and,
wherein the palladium metal catalyst has a surface enrichment value of from at least 6.5 to at most 150; and,
wherein the platinum metal catalyst has a surface enrichment value of from at least 1.5 to at most 150, and,
wherein the surface enrichment value (SEV) is determined from the following formula (I):

$$SEV=(XPS\ wt.\ \%-ICP\ wt.\ \%)/ICP\ wt.\ \%;\quad (I)$$

wherein XPS wt. % is the X-ray photoelectron spectroscopy (XPS) measurement and ICP wt. % is the inductively coupled plasma (ICP) measurement of the precious metal content in weight percent of said catalyst.

2. The catalyst according to claim 1,
wherein the palladium metal catalyst has a surface enrichment value of at least 8; and, wherein the palladium metal catalyst has a surface enrichment value of at most 120; and,
wherein the platinum metal catalyst has a surface enrichment value of at least 2; and, wherein the platinum metal catalyst has a surface enrichment value of at most 120.

3. The catalyst according to claim 1, wherein the catalyst comprises palladium and/or platinum metal in an amount of between more than 1.0 wt. % and 20 wt. %, based on the weight of the catalyst.

4. The catalyst according to claim 1, wherein the nanocrystallites have an average size of between 1 and 4 nm.

5. The catalyst according to claim 1, wherein the support is selected from the group consisting of silica, alumina, zirconia, titanium oxide, ceria, magnesium oxide, zinc oxide, metal silicates, metal aluminates, zeolites, carbon nanotubes, carbon nanofibres, graphitic carbon and activated carbon and combinations thereof.

6. The catalyst according to claim 1, wherein the Dv(90) particle size distribution of the powder support is between 1 and 500 micron.

7. The catalyst according to claim 1, wherein the BET surface area of the powder support is between 100 and 3000 m$^2$/g.

8. The catalyst according to claim 1, wherein the micropore surface area of the powder support is between 10 and 1000 m$^2$/g.

9. Process for preparing a precious metal catalyst, wherein said process comprises the steps of:

reducing a precious metal compound in an aqueous solution by contacting said solution with a reducing agent, a stabilizing agent and optionally a coordinating agent thereby forming a colloidal precious metal suspension;
contacting the suspension with a powder support at a pH value of between 9.5 and 11; and,
recovering the precious metal catalyst.

10. Process according to claim 9, wherein the precious metal is selected from platinum, palladium, iridium, rhodium, ruthenium, silver, gold and combinations thereof.

11. Process according to claim 9, wherein the suspension is contacted with a powder support at a pH value of between 9.5 and 10.5.

12. Process according to claim 9, wherein a coordinating agent is used in the reduction step of said process when the precious metal compound to be reduced is a palladium and/or gold metal compound, optionally in combination with one or more other precious metal compounds.

13. Process according to claim 9, wherein the reducing agent is selected from the group consisting of a quaternary ammonium salt, sodium formate, formic acid, sodium citrate, citric acid, hydrazine, $C_1$-$C_4$ alcohols, diols, polyols, borohydrides, formaldehyde, hypophosphite, metal alkalydes, hydrogen and combinations thereof;
wherein the stabilizing agent is selected from the group consisting of a quaternary ammonium salt, donor ligands, polymers, surfactants and combinations thereof; and,
wherein the coordinating agent is urea and/or ammonia.

14. Process according to claim 9, wherein the support is selected from the group consisting of silica, alumina, zirconia, titanium oxide, ceria, magnesium oxide, zinc oxide, metal silicates, metal aluminates, zeolites, carbon nanotubes, carbon nanofibres, graphitic carbon and activated carbon and combinations thereof.

15. A precious metal catalyst obtainable by the process of claim 9.

16. A process, comprising performing a reaction in the presence of a precious metal catalyst according to claim 15, wherein the reaction is a hydrogenation/dehydrogenation, isomerization, oxidation, hydrogenolysis or hydro-dewaxing reaction.

17. The catalyst according to claim 1, wherein the nanocrystallites of at least one precious metal are edge-coated on the powder support.

18. The process according to claim 9, wherein the precious metal suspension is edge-coated on the powder support.

19. The precious metal catalyst according to claim 9, wherein the stabilizing agent is a quaternary ammonium salt.

20. The process according to claim 9, wherein the coordinating agent is urea.

* * * * *

UNITED STATES PATENT AND TRADEMARK OFFICE
CERTIFICATE OF CORRECTION

PATENT NO. : 10,258,967 B2
APPLICATION NO. : 15/559458
DATED : April 16, 2019
INVENTOR(S) : Peter Witte et al.

Page 1 of 1

It is certified that error appears in the above-identified patent and that said Letters Patent is hereby corrected as shown below:

In the Specification

In Column 2, Line 3, delete "Chem Cat Chem." and insert -- ChemCatChem. --, therefor.

In Column 4, Line 35, delete "1 s-signal" and insert -- 1s- signal --, therefor.

Signed and Sealed this
Fourteenth Day of April, 2020

Andrei Iancu
*Director of the United States Patent and Trademark Office*